US010124175B2

United States Patent

(12) United States Patent
Berthiaume et al.

(10) Patent No.: US 10,124,175 B2
(45) Date of Patent: *Nov. 13, 2018

(54) DELIVERY SYSTEM ASSEMBLIES FOR IMPLANTABLE MEDICAL DEVICES

(71) Applicant: Medtronic, Inc., Minneapolis, MN (US)

(72) Inventors: William A Berthiaume, Santa Rosa, CA (US); H Allan Steingisser, Santa Rosa, CA (US); Don H Tran, Novato, CA (US); Erik Griswold, Penngrove, CA (US); Brent L Locsin, San Francisco, CA (US); James C Allan, Boise, ID (US)

(73) Assignee: Medtronic, Inc., Minneapolis, MN (US)

( * ) Notice: Subject to any disclaimer, the term of this patent is extended or adjusted under 35 U.S.C. 154(b) by 373 days.

This patent is subject to a terminal disclaimer.

(21) Appl. No.: 14/943,870

(22) Filed: Nov. 17, 2015

(65) Prior Publication Data

US 2016/0067503 A1 Mar. 10, 2016

Related U.S. Application Data

(62) Division of application No. 13/298,821, filed on Nov. 17, 2011, now Pat. No. 9,216,293.

(51) Int. Cl.
*A61M 29/00* (2006.01)
*A61N 1/372* (2006.01)
(Continued)

(52) U.S. Cl.
CPC ........ *A61N 1/37205* (2013.01); *A61B 5/0422* (2013.01); *A61B 5/6869* (2013.01);
(Continued)

(58) Field of Classification Search
CPC ............ A61B 5/6869; A61B 2560/066; A61B 5/6882; A61B 5/0422; A61N 1/37205;
(Continued)

(56) References Cited

U.S. PATENT DOCUMENTS

| | | |
|---|---|---|
| 3,835,864 A | 9/1974 | Rasor et al. |
| 3,943,936 A | 3/1976 | Rasor et al. |

(Continued)

FOREIGN PATENT DOCUMENTS

| | | |
|---|---|---|
| CN | 1870950 A | 11/2006 |
| CN | 101779992 A | 7/2010 |

(Continued)

OTHER PUBLICATIONS

English translation of Chinese Office Action, dated Sep. 29, 2015, 14 pages.

(Continued)

*Primary Examiner* — Richard Louis

(57) ABSTRACT

An inner subassembly of a delivery system assembly extends within a lumen of an elongate outer tube of the assembly, and includes a flared distal end, which is preferably configured to conform to a proximal end of an implantable medical device; a distal-most portion of the outer tube is sized to contain both the flared distal end and an entirety of the medical device. The inner subassembly includes a core, an elongate pull-wire, extending along the core, and a sheath surrounding the pull-wire and the core; the sheath includes a slot opening that allows the pull-wire to pass laterally therethrough. The assembly preferably has a preformed curvature along a length of the sheath, and the slot opening extends along the pre-formed curvature. The outer tube is longitudinally moveable relative to the inner subassembly, for example, to deploy the medical device.

9 Claims, 4 Drawing Sheets

(51) Int. Cl.

| | |
|---|---|
| ***A61B 5/00*** | (2006.01) |
| ***A61B 5/042*** | (2006.01) |
| ***A61N 1/375*** | (2006.01) |
| ***A61M 25/01*** | (2006.01) |

(52) U.S. Cl.
CPC .... *A61M 25/0136* (2013.01); *A61M 25/0147* (2013.01); *A61N 1/3756* (2013.01); *A61B 5/6882* (2013.01); *A61B 2560/066* (2013.01)

(58) Field of Classification Search
CPC ............ A61N 1/3756; A61M 25/0136; A61M 25/0147
See application file for complete search history.

(56) References Cited

U.S. PATENT DOCUMENTS

| | | | |
|---|---|---|---|
| RE30,366 | E | 8/1980 | Rasor et al. |
| 4,245,624 | A | 1/1981 | Komiya |
| 4,676,249 | A | 6/1987 | Arenas et al. |
| 5,040,543 | A | 8/1991 | Badera et al. |
| 5,090,422 | A | 2/1992 | Dahl et al. |
| 5,147,379 | A | 9/1992 | Sabbaghian et al. |
| 5,170,803 | A | 12/1992 | Hewson et al. |
| 5,267,982 | A | 12/1993 | Sylvanowicz |
| 5,334,160 | A | 8/1994 | Ellis |
| 5,431,696 | A | 7/1995 | Atlee, III |
| 5,643,231 | A | 7/1997 | Lurie et al. |
| 5,662,119 | A | 9/1997 | Brennen et al. |
| 5,827,201 | A | 10/1998 | Samson et al. |
| 5,873,842 | A | 2/1999 | Brennen et al. |
| 5,951,585 | A | 9/1999 | Cathcart et al. |
| 6,074,379 | A | 6/2000 | Prichard |
| 6,102,890 | A | 8/2000 | Stivland et al. |
| 6,408,214 | B1 | 6/2002 | Williams et al. |
| 6,485,440 | B1 | 11/2002 | Gardeski |
| 6,873,870 | B2 | 3/2005 | Ferek-Petric |
| 7,101,361 | B2 | 9/2006 | Gardeski |
| 7,241,257 | B1 | 7/2007 | Ainsworth et al. |
| 7,369,901 | B1 | 5/2008 | Morgan et al. |
| 7,444,180 | B2 | 10/2008 | Kuzma et al. |
| 7,532,933 | B2 | 5/2009 | Hastings et al. |
| 7,824,367 | B2 | 11/2010 | Accisano et al. |
| 7,840,281 | B2 | 11/2010 | Kveen et al. |
| 7,857,819 | B2 | 12/2010 | Jaax et al. |
| 7,967,798 | B2 | 6/2011 | Reydel et al. |
| 8,504,156 | B2 | 8/2013 | Bonner et al. |
| 8,721,587 | B2 | 5/2014 | Berthiaume et al. |
| 8,945,145 | B2 | 2/2015 | Tran et al. |
| 8,945,146 | B2 | 2/2015 | Steingisser et al. |
| 2002/0165537 | A1 | 11/2002 | Kelley et al. |
| 2003/0093059 | A1 | 5/2003 | Griffin et al. |
| 2003/0181855 | A1 | 9/2003 | Simpson et al. |
| 2004/0116994 | A1 | 6/2004 | De Bellis |
| 2004/0210211 | A1 | 10/2004 | Devens, Jr. et al. |
| 2005/0090834 | A1 | 4/2005 | Chiang et al. |
| 2005/0090890 | A1 | 4/2005 | Wu et al. |
| 2005/0267555 | A1 | 12/2005 | Marnfeldt et al. |
| 2005/0272975 | A1 | 12/2005 | McWeeney et al. |
| 2006/0004305 | A1 | 1/2006 | George et al. |
| 2006/0030923 | A1 | 2/2006 | Gunderson |
| 2006/0161211 | A1 | 7/2006 | Thompson et al. |
| 2006/0200221 | A1 | 9/2006 | Malewicz |
| 2006/0229698 | A1 | 10/2006 | Larson et al. |
| 2006/0241732 | A1 | 10/2006 | Denker et al. |
| 2007/0073389 | A1 | 3/2007 | Bolduc et al. |
| 2007/0088232 | A1 | 4/2007 | Corradini |
| 2007/0088323 | A1 | 4/2007 | Campbell et al. |
| 2007/0088418 | A1 | 4/2007 | Jacobson |
| 2007/0150037 | A1 | 6/2007 | Hastings et al. |
| 2007/0219551 | A1 | 9/2007 | Honour et al. |
| 2007/0250150 | A1 | 10/2007 | Pal et al. |
| 2007/0270932 | A1 | 11/2007 | Headley et al. |
| 2008/0021532 | A1 | 1/2008 | Kveen et al. |
| 2008/0039904 | A1 | 2/2008 | Bulkes et al. |
| 2008/0294216 | A1 | 11/2008 | Jarverud et al. |
| 2009/0005830 | A1 | 1/2009 | Zhu et al. |
| 2009/0005846 | A1 | 1/2009 | Zhu et al. |
| 2009/0069885 | A1 | 3/2009 | Rahdert et al. |
| 2009/0099641 | A1 | 4/2009 | Wu et al. |
| 2009/0182268 | A1 | 7/2009 | Thielen et al. |
| 2009/0254168 | A1 | 10/2009 | Parker et al. |
| 2010/0030294 | A1 | 2/2010 | Wong et al. |
| 2010/0198288 | A1 | 8/2010 | Ostroff |
| 2010/0204766 | A1 | 8/2010 | Zdeblick et al. |
| 2010/0274187 | A1 | 10/2010 | Argentine |
| 2011/0139754 | A1 | 6/2011 | Romanowski et al. |
| 2011/0144572 | A1 | 6/2011 | Kassab et al. |
| 2011/0251660 | A1 | 10/2011 | Griswold |
| 2011/0251662 | A1 | 10/2011 | Griswold et al. |
| 2012/0053651 | A1 | 3/2012 | Zhu et al. |
| 2012/0172892 | A1 | 7/2012 | Grubac et al. |
| 2012/0245665 | A1 | 9/2012 | Friedman et al. |
| 2012/0245679 | A1 | 9/2012 | Solem |
| 2013/0103047 | A1 | 4/2013 | Steingisser et al. |
| 2013/0131693 | A1 | 5/2013 | Berthiaume et al. |

FOREIGN PATENT DOCUMENTS

| | | | |
|---|---|---|---|
| WO | 01/83017 | A1 | 11/2001 |
| WO | 03/032807 | A2 | 4/2003 |
| WO | 2006/099425 | | 9/2006 |
| WO | 2012/092074 | A1 | 7/2012 |

OTHER PUBLICATIONS

Chinese Office Action, dated Sep. 29, 2015, 9 pages, Chinese version.

Notification Concerning Transmittal of International Preliminary Report on Patentability, mailed May 30, 2014, 9 pages.

PCT/US2012/065229 Notification of Transmittal of the International Search Report and the Written Opinion of the International Searching Authority, or the Declaration, dated Feb. 11, 2013, 12 pages.

PCT/US2012/056029 Notification of Transmittal of the International Search Report and the Written Opinion of the International Searching Authority, or the Declaration, dated Mar. 7, 2013, 14 pages.

Chinese Office Action, serial No. 201280058471.7, dated Apr. 3, 2015, 7 pages.

Translation of Chinese Office Action, serial No. 201280058471.7, dated Apr. 3, 2015, 5 pages.

(PCT/US2012/060015) PCT Notification of Transmittal of the International Search Report and the Written Opinion of the International Searching Authority.

(PCT/US2012/065264) PCT Notification of Transmittal of the International Search Report and the Written Opinion of the International Searching Authority.

(PCT/US2012/049264) PCT Notification of Transmittal of the International Search Report and the Written Opinion of the International Searching Authority.

DELIVERY SYSTEM ASSEMBLIES FOR IMPLANTABLE MEDICAL DEVICES

CROSS-REFERENCE TO RELATED APPLICATIONS

This application is a divisional of U.S. patent application Ser. No. 13/298,821 (now allowed), filed Nov. 17, 2011 entitled "DELIVERY SYSTEM ASSEMBLIES FOR IMPLANTABLE MEDICAL DEVICES", which is herein incorporated by reference in its entirety.

The present application is related to the following co-pending and commonly assigned United States patent applications: application Ser. No. 13/239,990 (issued as U.S. Pat. No. 8,945,145), which is entitled DELIVERY SYSTEM ASSEMBLIES FOR IMPLANTABLE MEDICAL DEVICES, and which was filed on Sep. 22, 2011 application Ser. No. 13/279,835 (issued as U.S. Pat. No. 8,945,146), which is entitled DELIVERY SYSTEM ASSEMBLIES AND ASSOCIATED METHODS FOR IMPLANTABLE MEDICAL DEVICES, and which was filed on Oct. 24, 2011; application Ser. No. 13/298,973 (issued as U.S. Pat. No. 8,721,587), which is entitled DELIVERY SYSTEM ASSEMBLIES AND ASSOCIATED METHODS FOR IMPLANTABLE MEDICAL DEVICES, and which was filed on Nov. 17, 2011; and application Ser. No. 13/219,279 (issued as U.S. Pat. No. 8,504,156), which is entitled HOLDING MEMBERS FOR IMPLANTABLE CARDIAC STIMULATION DEVICES, and which was filed on Aug. 26, 2011.

FIELD OF THE DISCLOSURE

The present invention pertains to delivery system assemblies for implantable medical devices, and more particularly to delivery system assemblies configured to facilitate percutaneous transvenous deployment of relatively compact implantable medical devices.

BACKGROUND

The traditional implantable cardiac pacemaker includes a pulse generator device to which one or more flexible elongate lead wires are coupled. The device is typically implanted in a subcutaneous pocket, remote from the heart, and each of the one or more lead wires extends therefrom to a corresponding electrode, coupled thereto and positioned at a pacing site, either endocardial or epicardial. Mechanical complications and/or MRI compatibility issues, which are sometimes associated with elongate lead wires and well known to those skilled in the art, have motivated the development of cardiac pacing devices that are wholly contained within a relatively compact package for implant in close proximity to the pacing site, for example, within the right ventricle (RV) of the heart. With reference to FIG. 1, such a device 100 is illustrated, wherein pace/sense electrodes 111, 112 are formed on an exterior surface of an enclosure that hermetically contains a pulse generator including pulse generator electronics and a power source. FIG. 1 illustrates a fixation member 115 mounted to an end of the enclosure of device 100, in proximity to electrode 111, in order to fix, or secure electrode 111 against the endocardial surface in the apex of the RV. The enclosure is preferably formed from a biocompatible and biostable metal such as titanium, which may be overlaid with an insulative layer, for example, medical grade polyurethane or silicone, except where electrode 112 is formed as an exposed portion of the enclosure. A hermetic feedthrough assembly (not shown), such as any known to those skilled in the art, couples electrode 111 to the pulse generator contained within the enclosure of device 100.

FIG. 1 further illustrates a distal portion of a standard guiding catheter 150 having been maneuvered up through the inferior vena cava (IVC) and into the RV from the right atrium (RA), according to methods known in the art of interventional cardiology. Although catheter 150 may be employed to deliver device 100 to the RV, for implant, more sophisticated delivery systems that facilitate improved navigation and deployment more suitable for relatively compact implantable devices, like device 100, are desired.

SUMMARY

A delivery system assembly, according to embodiments of the present invention, includes an inner subassembly and an outer subassembly and is deflectable and retractable for deployment of an implantable medical device. An elongate core of the inner subassembly extends within a lumen of an elongate outer tube of the outer subassembly, and the inner subassembly further includes an elongate pull-wire extending along the core, and a sheath, which extends around the pull-wire and the core, within the lumen formed by the outer tube. The elongate core preferably includes a flared distal end, which is conformable to a proximal end of the medical device; and a distal-most portion of the outer tube, is preferably sized to contain both the flared distal end of the core and an entirety of the medical device.

The pull-wire may be actuated to deflect the flared distal end of the core along with distal-most portion of the outer tube, so that a distal opening of the outer tube lumen may be directed toward a target implant site for deployment of the contained medical device therethrough, for example, by retraction of the outer tube, relative to the inner subassembly. The sheath preferably includes a slot opening that is located and sized to allow the pull-wire to pass laterally therethrough. According to some preferred embodiments, the assembly has a pre-formed curvature, along a length of the sheath, to orient the distal-most portion of the outer tube for navigation within a venous system of a patient, and the slot opening extends along a length of the pre-formed curvature.

Deployment of the medical device may be accomplished by moving the outer tube in a proximal direction, between first and second positions, relative to the inner subassembly, for example, via a first control member of a handle of the delivery system. When the outer tube is in the first position, the above-described deflection may be actuated, for example, via a second control member of the handle; and, when the outer tube is moved proximally, or retracted toward the second position, a fixation member of the medical device becomes exposed, to engage with tissue in proximity to the target implant site.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments will hereinafter be described in conjunction with the appended drawings wherein like numerals denote like elements, and.

DETAILED DESCRIPTION

The following detailed description is exemplary in nature and is not intended to limit the scope, applicability, or configuration of the invention in any way. Rather, the following description provides practical examples, and those skilled in the art will recognize that some of the examples may have suitable alternatives.

Figures 2A, 2B, 2C:
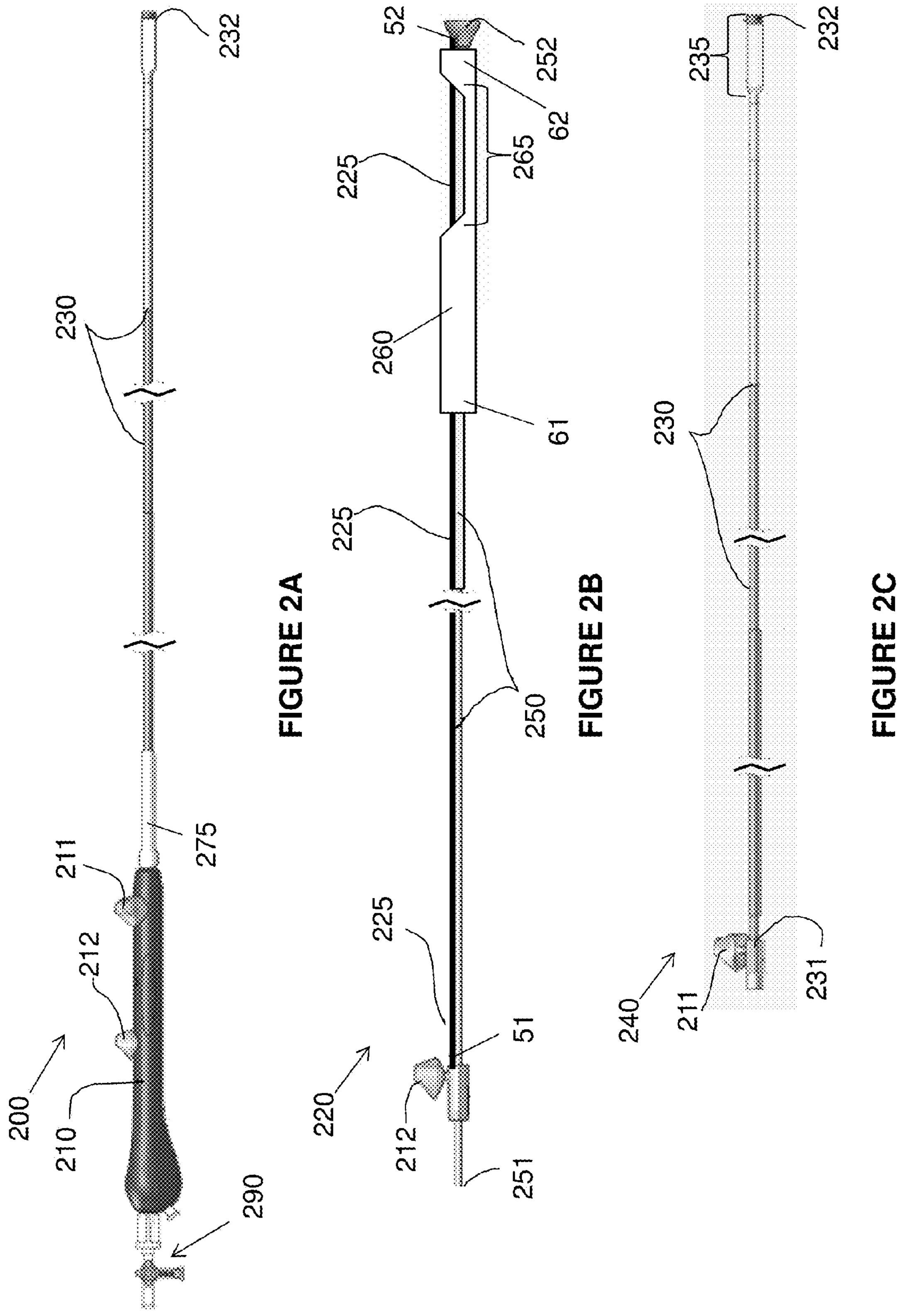
FIG. 2A is a plan view of a delivery system assembly, according to some embodiments.
FIGS. 2B-C are plan views of inner and outer subassemblies, respectively, of the system assembly shown in FIG. 2A, according to some embodiments.

FIG. 2A is a plan view of a delivery system assembly 200, according to some embodiments; and FIGS. 2B-C are plan views of an inner subassembly 220 and an outer subassembly 240, respectively, of system assembly 200. FIG. 2A illustrates system assembly including a handle 210 and an elongate outer tube 230 extending from handle 210 to a distal end 232 thereof. According to the illustrated embodiment, outer tube 230 forms a lumen (not shown) in which inner subassembly 220 extends; and, it should be understood that, the lumen formed by outer tube 230 preferably has a proximal opening at proximal end 231 and a distal opening at distal end 232. FIG. 2B illustrates inner subassembly 220 including an elongate core 250, an elongate pull-wire 225, which extends along core 250, and a sheath 260, which surrounds pull-wire 225 and core 250, for example, over a length of between approximately 12 cm and approximately 18 cm. FIG. 2A further illustrates handle 210 including a first control member 211 and a second control member 212. With reference to FIG. 2C, a proximal end 231 of outer tube 230 is shown coupled to first control member 211, for example, by a UV cure adhesive; and, with reference to FIG. 2B, a proximal end of pull-wire 51 is shown coupled to second control member 212, for example, by a UV cure adhesive. According to an exemplary embodiment, pull-wire 225 has a diameter of approximately 0.009 inch (~0.23 mm) and is formed from medical grade 304 stainless steel, which is preferably coated with a fluoropolymer such as polytetrafluoroethylene (PTFE). According to FIG. 2B, core 250 extends proximally, beyond proximal end 231 of outer tube and second control member 212, to a proximal end 251 thereof, which is preferably fixed within handle 210 and may be coupled to a luer fitting (not shown), to which a stop cock 290 is shown coupled in FIG. 2A. According to some preferred embodiments, control members 211, 212 are slidable along handle 210, such that: first control member 211 actuates longitudinal movement of outer tube, to retract outer tube 230, relative to inner subassembly 220 and handle 210 (FIG. 3B); and second control member 212 actuates pull-wire 225 to deflect a flared distal end 252 of core 250, which, in turn, deflects distal end 232 of outer tube 230 (FIG. 3A), for example, toward a target implant site, prior to the retraction of outer tube 230.

Figure 3A:
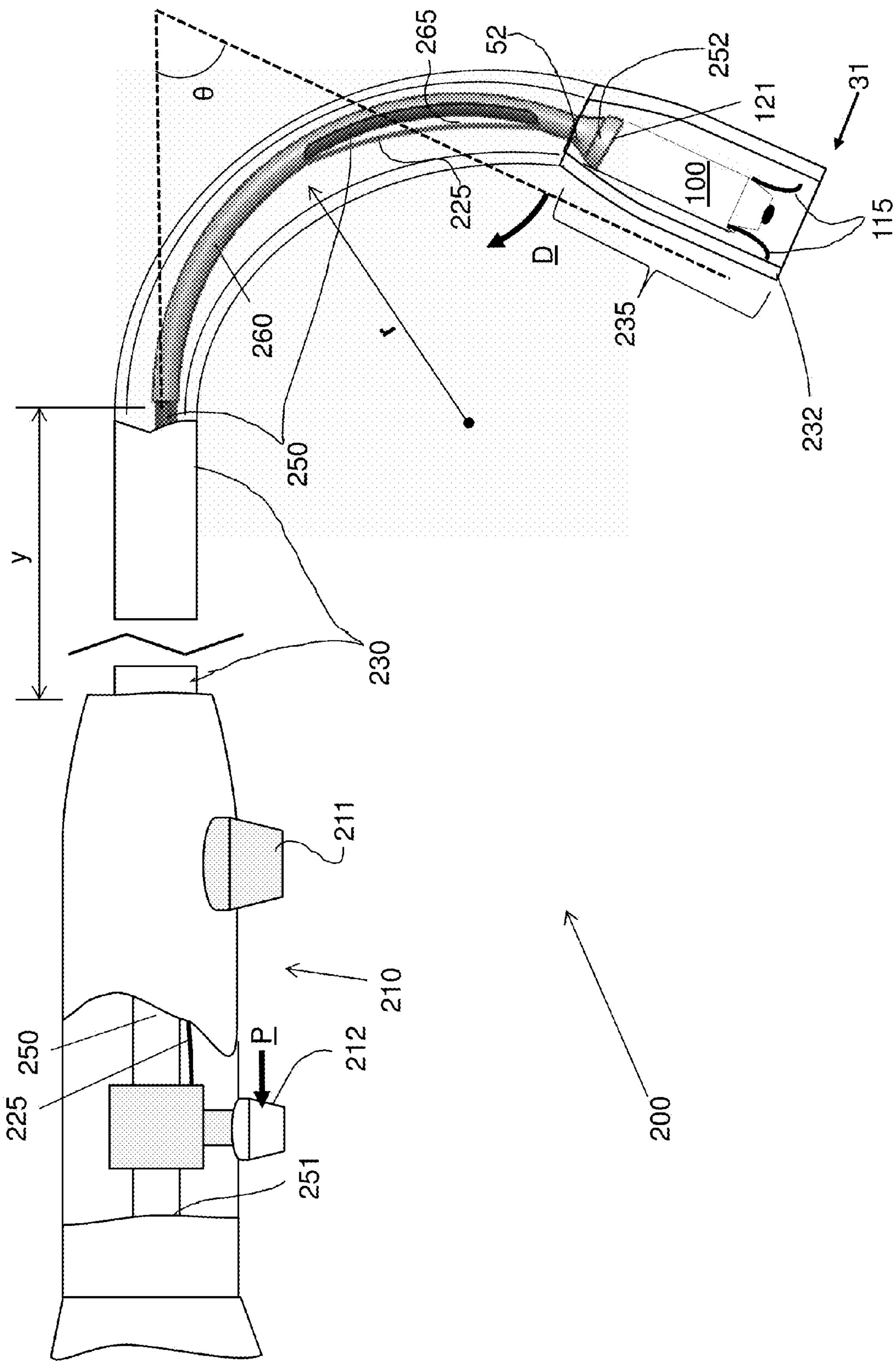
FIG. 3A is a plan view, including cut-away sections, of the delivery system assembly, according to some alternate embodiments and with an outer tube thereof in a first position.

Flared distal end 252 of core 250 is preferably configured to conform to a proximal end 121 of implantable medical device 100, for example, as illustrated in FIG. 3A, and, with further reference to FIG. 3A, the lumen of outer tube 230, along a length of a distal-most portion 235 of outer tube 230, is sized to contain both flared distal end 252 and device 100 together, in order to deliver device 100 into proximity with the target implant site. According to some embodiments, the conforming configuration of distal end 252 can help to retain device 100 within distal-most portion 235 of outer tube 230 during navigation of delivery system assembly 200 and prior to deployment of device 100 therefrom. According to an exemplary embodiment, distal-most portion 235 has an inner diameter of approximately 0.275 inch (~0.7 cm) and an outer diameter of approximately 0.3 inch (~0.8 cm). Although FIGS. 2C and 3A illustrate distal-most portion 235 being enlarged from a remainder of outer tube 230, for example, over a length of approximately 3.5 cm (~1.4 inch), according to alternate embodiments, an outer diameter along a more significant length up to an entire length of outer tube 230 may be the same as that of the distal-most portion. According to some preferred embodiments, flared distal end 252 of core 250 is radiopaque and distal end 232 of outer tube 230 is fitted with a radiopaque marker, so that the retraction of outer tube 230, relative to flared distal end 252, which will be described in greater detail below, can be observed via fluoroscopy. According to an exemplary embodiment, flared distal end 252 is formed from a polyether block amide, for example, PEBAX® 7033, with a radiopaque Barium sulfate filler; and distal-most portion 235 of outer tube 230 is formed from a polyether block amide, for example, PEBAX® 7233, which, at distal end 232, includes a radiopaque band of 75% Tungsten and 25% PEBAX® 6033 sandwiched between layers of the PEBAX® 7233.

FIGS. 2B and 3A illustrate sheath 260 including a slot opening 265 that is located and sized to allow pull-wire 225 to pass laterally therethrough. A length of slot 265 may be between approximately 1 cm and approximately 5 cm, preferably between approximately 2.5 cm and approximately 3 cm. FIGS. 2B and 3A further illustrates a distal end 62 of sheath 260 coupled to core 250 in close proximity to anchored distal end 52 of pull-wire 225, and a proximal end 61 of sheath 260 spaced apart, distally, from handle 210, for example, by a longitudinal distance y (FIG. 3A), which is between approximately 90 cm and approximately 100 cm.

Figure 1:
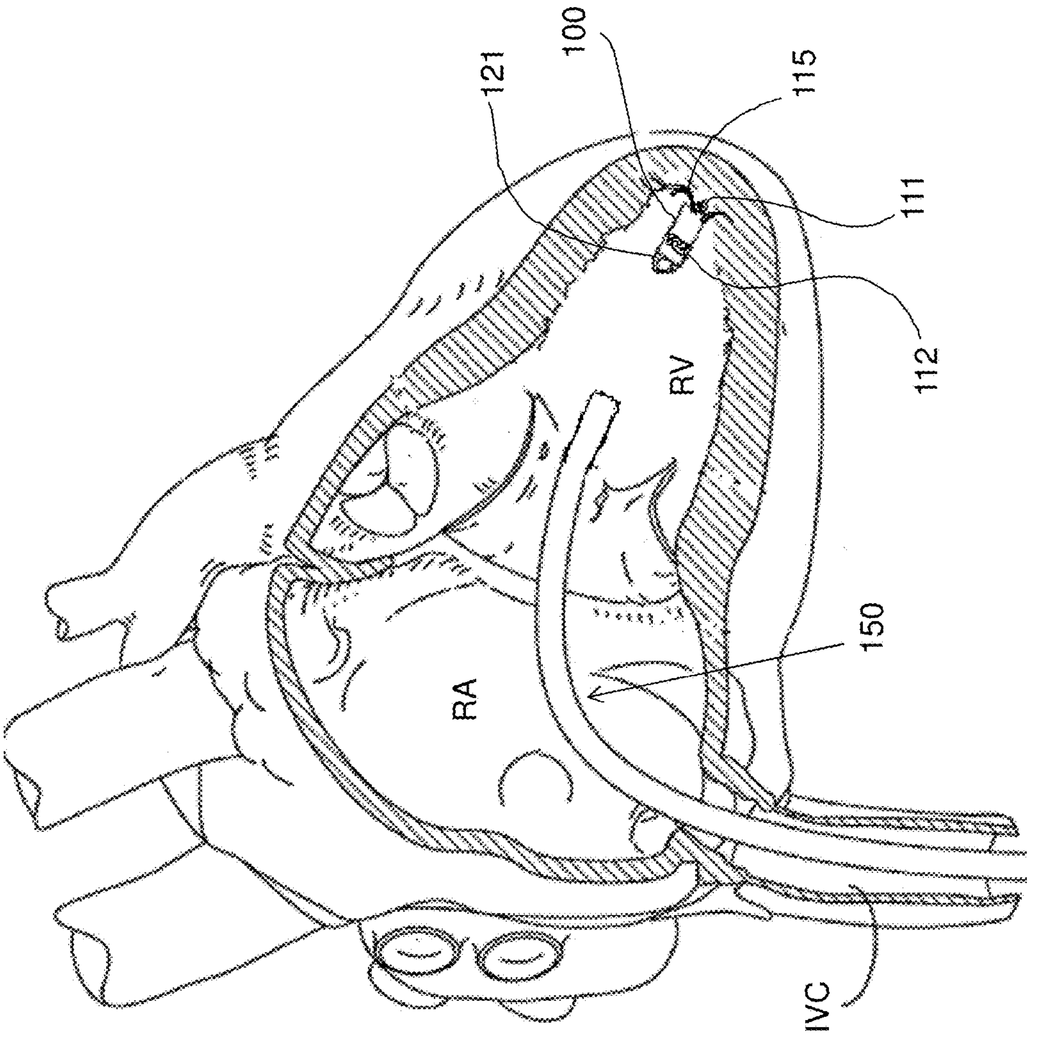
FIG. 1 is a schematic showing an example of an implanted cardiac stimulation device.

FIGS. 2A-C show assembly 200 extending along a relatively straight line, according to some embodiments, but, according to some preferred embodiments, assembly 200 has a pre-formed curvature along a length of sheath 260, for example, as illustrated in FIG. 3A, wherein the length may be between approximately 6 cm and approximately 20 cm. With reference to FIG. 3A, the pre-formed curvature extends about a radius r of between approximately 9 cm and approximately 13 cm, and orients distal-most portion 235 at an angle θ of approximately 120 degrees with respect to a length of assembly 200 that extends proximal to the pre-formed curve. The radius of curvature r and angle θ can facilitate the navigation of delivery system assembly 200 within a venous system of a patient, for example, by orienting distal-most portion 235 of outer tube 230 for passage from the RA, through the tricuspid valve, into the RV (FIG. 1). With further reference to FIG. 3A, pull-wire 225 is shown extending laterally through slot opening 265. According to the illustrated embodiment, when second control member 212 is moved, per arrow P, pull-wire 225 is actuated to deflect distal end 252 of core 250, along with distal end 232 of outer tube 230, per arrow D, into a tighter radius, for example, so that the distal opening of the lumen of outer tube 230 may be directed toward a target implant site for deployment of the contained medical device 100 therethrough, for example, by retraction of outer tube 230, relative to inner subassembly 200, as described below.

According to an exemplary embodiment, core 250 extends over a length of approximately 118 cm, from proximal end 251 to just proximal to flared distal end 252, has an outer diameter of approximately 0.112 inch (~2.85 mm), and is formed from a stainless steel braid (0.0012"×0.003"×70 PPI) surrounding a polyether block amide PEBAX® 7033 liner, and overlaid, along a proximal section (having a length of approximately 108 cm), with a layer of Trogamid® polyamide, and, along a distal section (having a length of approximately 10 cm), with a layer of Vestamid® polyamide. In this exemplary embodiment, sheath 260 is formed from a polyether block amide PEBAX® 5533, which has a durometer, on a shore D scale, of between approximately 50 and approximately 55. Although FIG. 2B shows a length of pull-wire 225, which extends proximally from sheath 260 to proximal end 51, unconstrained alongside core 250, according to some alternate embodiments, a lumen, for example, having a diameter of approximately 0.015 inch (~0.38 mm), extends along the wall of core 250 to contain this length of pull-wire 225. FIGS. 2B and 3A show a distal end 52 of pull-wire 225 anchored to core 250 in proximity to flared distal end 252, for example, by thermal bonding within the polymer melt that forms the junction between sheath 260 and flared distal end 252. Although not shown, distal end 52 of pull-wire 225 may be terminated by a ring or band that is thermally bonded within, or in close proximity to the junction between sheath 260 and distal end 252. For those embodiments in which assembly 200 has the pre-formed curvature, the curvature may be formed by heat setting, according to methods known to those skilled in the art of catheter construction. The curvature may be pre-formed into inner subassembly 220, prior to inserting subassembly 220 within the lumen of outer tube 230, or the curvature may be pre-formed into outer tube 230, prior to assembling inner subassembly 220 therein.

The construction of outer tube 230 may be any suitable type known in the art to achieve a graduated flexibility that accommodates deflection in response to the deflection of core 250, for example, as described above, and to achieve the necessary pushability and torque transfer that facilitates the maneuverability of delivery system assembly 200 to a target implant site, as will be described in greater detail below. According to an exemplary embodiment, outer tube 230 includes a braid reinforced liner, for example, PEBAX® 6333 with a stainless steel braid (i.e. 0.0018"×0.008"×45 PPI) extending from proximal end 231 to just proximal to distal-most portion 235 of outer tube 230; a proximal segment of the shaft is overlaid with PEBAX® 7033 and extends over a length of approximately 92 cm (a proximal portion of which length is always contained within handle 210); an intermediary segment of the shaft is overlaid with PEBAX®4033 and extends distally from the proximal segment over a length of approximately 10 cm; and a distal segment of the shaft is overlaid with PEBAX® 3533 and extends distally from the intermediary segment, over a length of approximately 3 cm, to just proximal to the distal-most portion. Outer and inner diameters of outer tube 230, along the above-described segments, may be approximately 0.187 inch (~4.75 mm) and approximately 0.154 inch (~3.91 mm), respectively.

Figure 3B:
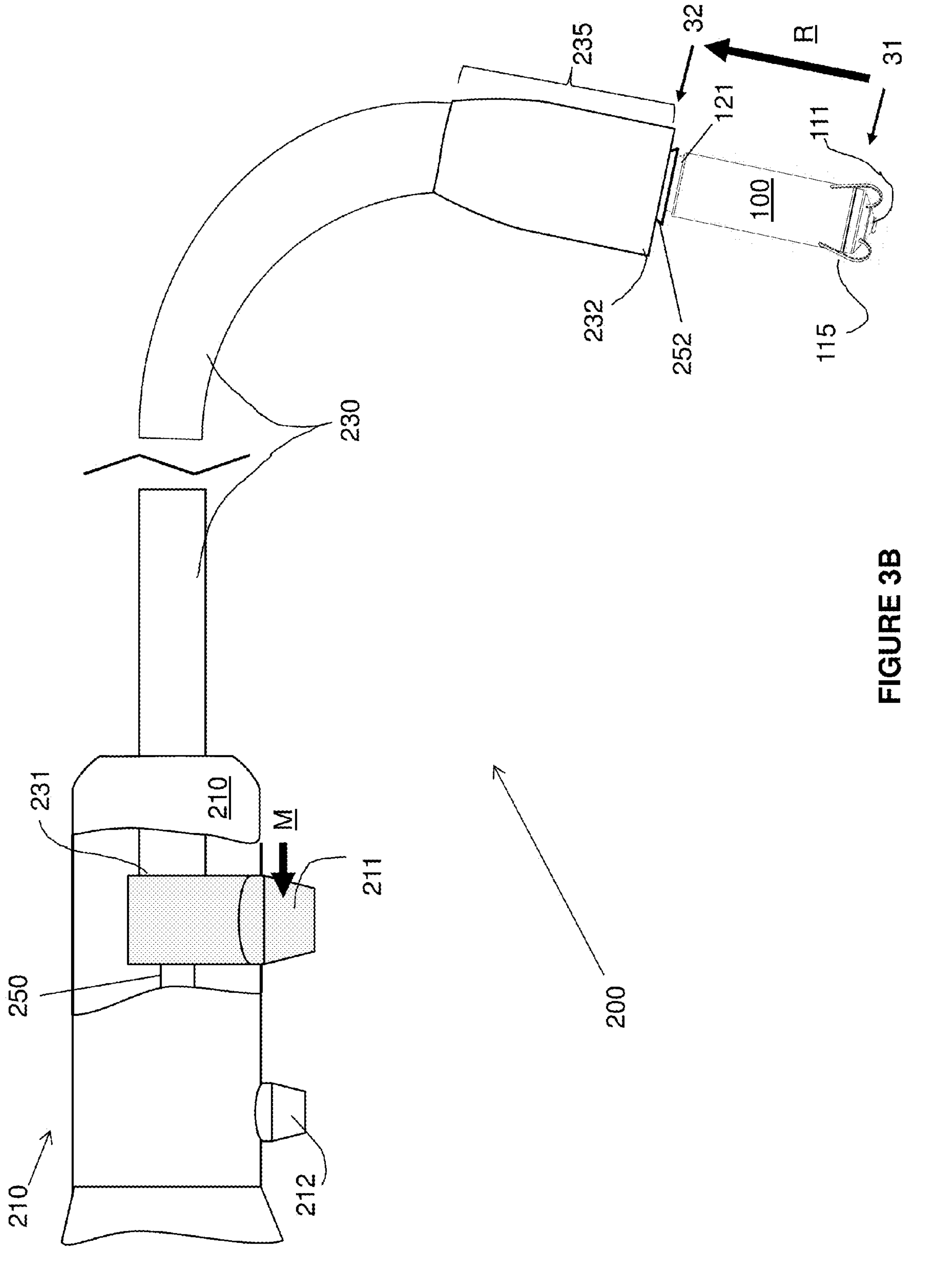
FIG. 3B is a plan view, including a cut-away section, of the assembly of FIG. 3A with the outer tube in a second position.

With further reference to FIG. 3A, while delivery system assembly 200 is being advanced within a patient's venous system and maneuvered into proximity to the target implant site, for example, within the RV (FIG. 1), and while second control member 212 is moved, per arrow P, to actuate the deflection, per arrow D, via pull-wire 225, outer tube 230 generally remains in a first position 31 relative to core 250, so that an entirety of device 100 is contained within distal-most portion 235. According to some preferred embodiments, a longitudinal distance between handle 210 and distal end 231 of outer tube 230, when outer tube 230 is in first position 31, is between approximately 103 cm and approximately 107 cm, for example, to reach the RV from a femoral access site. Once deflected, so that distal end 232 of outer tube 230 is adjacent the target implant site, first control member 211 is moved, per arrow M, as illustrated in FIG. 3B, to retract outer tube 230 longitudinally, relative to core 250, from first position 31 to a second position 32, per arrow R. According to the illustrated embodiment, the retraction of outer tube 230 exposes fixation member 115 of device 100, which passes outside distal-most portion 235, through the distal opening of the lumen of outer tube 230, for engagement within tissue at the target implant site. According to some embodiments, an O-ring type seal member (i.e. silicone; not shown), which may be lubricated, for example, with silicone oil, forms a dynamic sealing interface between outer tube 230 and core 250 within handle 210, in proximity to first control member 211.

The above-described conforming configuration of flared distal end 252 may help to retain a temporary connection between device 100 and delivery system assembly 200 until fixation member 115 becomes engaged with the tissue; but, according to some preferred embodiments, device 100 is further secured to system assembly 200 by a tether, which is removably attached to proximal end 121 of device 100, for example, as described in the above-referenced related U.S. patent application Ser. No. 13/279,835, now issued as U.S. Pat. No. 8,945,146. Another of the above-referenced related applications, U.S. patent application Ser. No. 13/219,279, now issued as U.S. Pat. No. 8,504,156, describes some alternate configurations of proximal end 121 of device 100 that may be employed for tether attachment. Although FIG. 3A illustrates distal end 232 of outer tube 230 approximately aligned with flared distal end 252 of core 250, when outer tube 230 is in second position 32, second position 32 may be located more proximally, such that more of core 250 is exposed distal to distal end 232 of outer tube 230, or more distally, such that only fixation member 115 of device 100 is exposed. According to FIG. 3B, an entirety of device 100 is exposed when outer 230 is in second position 32; thus, a longitudinal distance between first position 31 and second position 32 may be as small as approximately 2 cm up to approximately 6 cm, depending on the length of device 100. Alternately, second position 32, as mentioned above, may be located to only expose a portion of device 100, for example, enough of fixation member 115 to secure device 100 at the implant site, in which case, the longitudinal distance between the first and second positions may be as small as approximately 0.5 cm to 1 cm.

With further reference to FIG. 2A, delivery system assembly 200 further includes an optional overlay 275, which is shown surrounding outer tube 230, in proximity to handle 210. Optional overlay 275 provides an enhanced interface between system assembly 200 and a valve of an introducer sheath, which is used to introduce system assembly 200 into the patient's venous system, to facilitate the above-described longitudinal movement of outer tube 230 relative to core 250 and handle 210. For example, the enhanced interface provides improved sealing and/or additional radial strength to counteract a compressive force of the valve, which, if the valve is a Tuohy Borst type, can be tightened down around system assembly 200 to different degrees depending upon the operator. Optional overlay 275 is preferably slidable over outer tube 230 so that overlay 275 may be repositioned with respect to handle 210 in order to coincide with the valve of the introducer sheath. According to an exemplary embodiment, optional overlay 275 is formed from a polyether block amide, for example, PEBAX® 7030, which may include a titanium oxide filler. Such an overlay is described in the above-referenced related U.S. patent application Ser. No. 13/239,990, now issued as U.S. Pat. No. 8,945,145, the description of which is hereby incorporated by reference. It should be noted that, although not shown, delivery system assembly 200 may alternately, or in addition, include an outer stability sheath like the stability sheath (250) that is described in the immediately aforementioned related application, the description of which is also incorporated by reference.

In the foregoing detailed description, the invention has been described with reference to specific embodiments. However, it may be appreciated that various modifications and changes can be made without departing from the scope of the invention as set forth in the appended claims.

The invention claimed is:

1. A delivery system assembly facilitating deployment of an implantable medical device, the assembly comprising:

a handle including a first control member and a second control member;

an elongate core extending from a proximal end thereof to a flared distal end thereof, the proximal end being fixed within the handle, and the flared distal end being configured to conform to a proximal end of the medical device;

an elongate outer tube forming a lumen in which the core extends, the outer tube including a proximal end, a distal end and a distal-most portion extending proximally from the distal end of the outer tube, the lumen having a proximal opening at the proximal end of the outer tube and a distal opening at the distal end of the outer tube, the proximal end of the outer tube being coupled to the first control member of the handle, the outer tube being longitudinally moveable, with respect to the handle and the core, between first and second positions, by means of the first control member, the flared distal end of the core being located within the distal-most portion, when the outer tube is in the first position, and the lumen of the outer tube, along a length of the distal-most portion, being sized to contain both the flared distal end of the core and an entirety of the medical device, together, within the distal-most portion, when the outer tube is in the first position;

an elongate pull-wire extending along the core and within the lumen of the outer tube, the pull-wire including a proximal end and a distal end, the proximal end of the pull-wire being coupled to the second control member of the handle and the distal end of the pull-wire being anchored to the core in close proximity to the flared distal end thereof; and a sheath extending around the pull-wire and the core and within the lumen of the outer tube, the sheath including a distal end, a proximal end and a slot opening located therebetween, the distal end of the sheath being coupled to the core in close proximity to the anchored distal end of the pull-wire, the proximal end of the sheath being located within the lumen of the outer tube and spaced apart, distally, from the handle, and the slot opening being located and sized to allow the pull-wire to pass laterally therethrough;

wherein, when the outer tube is in the second position, the flared distal end of the core is located in proximity to the distal end of the outer tube.

2. The assembly of claim 1, wherein a length of the slot opening of the sheath is between approximately 2.5 cm and approximately 3 cm.

3. The assembly of claim 1, wherein the sheath has a length of between approximately 12 cm and approximately 18 cm, and the proximal end of the sheath is spaced distally apart from the handle by a longitudinal distance of between approximately 90 cm and approximately 100 cm.

4. The assembly of claim 1, wherein the elongate core is formed from a braid reinforced polymer comprising a polyether block amide and a polyamide; and the sheath is formed from a polyether block amide having a hardness in a range of approximately 50 to approximately 55 on a shore D scale.

5. The assembly of claim 1, wherein the assembly has a pre-formed curvature along a length of the sheath, the curvature extending about a radius of between approximately 9 cm and approximately 13 cm, and the slot opening of the sheath extending along a length of the curvature.

6. The assembly of claim 1, wherein the flared distal end of the core is radiopaque.

7. The assembly of claim 1, wherein a longitudinal distance between the handle and the distal end of the outer tube, when the outer tube is in the first position, is between approximately 103 cm and approximately 107 cm.

8. The assembly of claim 1, wherein a longitudinal distance between the first position and the second position of the outer tube ranges from approximately 2 cm to approximately 6 cm.

9. The assembly of claim 1, further comprising a valve interface overlay surrounding the outer tube in proximity to the handle, the overlay being slidable over the outer tube for repositioning of the overlay with respect to the handle.

* * * * *